United States Patent
Kettunen et al.

(10) Patent No.: US 7,330,752 B2
(45) Date of Patent: Feb. 12, 2008

(54) PROCEDURE FOR DETECTION OF STRESS BY SEGMENTATION AND ANALYZING A HEART BEAT SIGNAL

(75) Inventors: Joni Kettunen, Saynatsalo (FI); Sami Saalasti, Jyvaskyla (FI)

(73) Assignee: Firstbeat Technologies Oy, Jyvaskyla (FI)

( * ) Notice: Subject to any disclaimer, the term of this patent is extended or adjusted under 35 U.S.C. 154(b) by 214 days.

(21) Appl. No.: 10/523,160

(22) PCT Filed: Aug. 18, 2003

(86) PCT No.: PCT/FI03/00608

§ 371 (c)(1),
(2), (4) Date: Jan. 27, 2005

(87) PCT Pub. No.: WO2004/016172

PCT Pub. Date: Feb. 26, 2004

(65) Prior Publication Data

US 2005/0256414 A1  Nov. 17, 2005

(30) Foreign Application Priority Data

Aug. 16, 2002  (FI) ............................. 20025039

(51) Int. Cl.
*A61B 5/04* (2006.01)
*A61B 5/083* (2006.01)

(52) U.S. Cl. .................. 600/513; 600/508; 600/509; 600/519; 600/520

(58) Field of Classification Search ........ 600/508–509, 600/513, 519–520
See application file for complete search history.

(56) References Cited

U.S. PATENT DOCUMENTS

| | | | |
|---|---|---|---|
| 5,267,568 A | 12/1993 | Takara | 600/500 |
| 5,419,338 A | 5/1995 | Sarma et al. | 600/516 |
| 5,713,367 A * | 2/1998 | Arnold et al. | 600/517 |
| 5,788,645 A * | 8/1998 | Swanson et al. | 600/516 |
| 5,891,044 A | 4/1999 | Golosarsky et al. | 600/509 |
| 5,902,250 A | 5/1999 | Verrier et al. | 600/515 |
| 6,104,947 A | 8/2000 | Heikkila et al. | 600/519 |
| 6,358,201 B1 | 3/2002 | Childre et al. | 600/300 |

OTHER PUBLICATIONS

Fukushima S. et al "A VR relax/refresh system employing physiological feedback". Trans. Inst. Electr. Eng. Jpn. C (Japan), Transactions of the Institute of Electrical Engineers of Japan, Part C, Feb. 1995, Japan. pp. 222-229, Inspec An: 4922327 Retrieved on Oct. 31, 2003.

* cited by examiner

*Primary Examiner*—Carl Layno
*Assistant Examiner*—Natasha Patel
(74) *Attorney, Agent, or Firm*—Fildes & Outland, P.C.

(57) ABSTRACT

A procedure for the detection of stress state is disclosed, wherein ambulatory heart beat signal is measured. In the first phase segments are defined from heart beat signal with a chosen rule for segmentation. Then at least one segment describing a physiological state with elevated cardiac activity due to physical workload and/or increased metabolic rate is identified and excluded, if exists, and segments other than the excluded segments are detected for a potential stress state, which is identified using a predetermined rule for the heart beat signal.

14 Claims, 5 Drawing Sheets

PROCEDURE FOR DETECTION OF STRESS BY SEGMENTATION AND ANALYZING A HEART BEAT SIGNAL

BACKGROUND OF THE INVENTION

1. Field of the Invention

The present innovation relates to procedure for the detection of stress state, wherein ambulatory heart period is measured and the derived signal is segmented into physiological states. The term "stress state" means herein also its opposite, "relaxation state".

2. Description of the Prior Art

Heart period is among the most commonly used parameters in physiological monitoring. The wide use of heart period is related, on the one hand, to the availability of electrocardiograph (ECG) acquisition device for noninvasive monitoring and, on the other hand, to central role of heart period in the autonomic nervous system function and sensitivity to several physiological states and conditions. Heart period (or, its reciprocal heart rate) forms a basis for different types of analyses and may be defined as the series of intervals between consecutive QRS-waveforms in the ECG-signal. Another method of deriving information on the time distance between consecutive heart beats is the detection of heart beat intervals from heart pulse signal.

The fact that heart period is a complex product of several physiological mechanisms poses a challenge to the use of heart period in applied contexts. This is especially the case within ambulatory measurement, that is, measurement that is performed within natural, free-living condition or field tests, outside of controlled laboratory environment and protocols. However, the multidetermined nature of the heart period may also potentate a derivation of additional physiological measures from the heart period signal by means of decomposing a series of heart periods into separate components that have a physiological interpretation.

It is well known that both branches of the autonomic nervous system (ANS), the sympathetic nervous system (SNS) and parasympathetic nervous system (PNS) influence heart rate. It is commonly known that the activity of the SNS and PNS produce, respectively, an increase and decrease in the heart rate level. It is therefore no surprising that much of the work on assessing physiological functions and states using information on heart beat signal often addresses changes in heart beat as stemming from the influence of SNS and/or PNS. Unfortunately, it is usually very difficult to determine precisely the effects of SNS and PNS on the heart rate, since it is often not apparent which branch of the ANS determines changes in heart rate and, in addition to these mechanisms, there are several other mechanisms altering the level of heart rate both directly and indirectly, many of which are not well-known.

The prior art has documented several research lines attempting to use heart rate variability (HRV) to quantify more selectively the activity of SNS and PNS. It has been documented that, especially the power of the so-called high frequency (HF) component of the HRV in the frequency region of 0.15-0.50 Hz provides information on the level of parasympathetic outflow to the heart. Unfortunately, although it has been claimed in some instances that the so-called low-frequency (LF) component of the HRV in the frequency region of 0.04-0.15 reflects SNS activity, the effects of SNS on HRV are rather unclear and it is known that several other mechanisms also influence HRV and especially the LF component, including PNS, hormonal responses, metabolic adjustments, and blood pressure control. Thus, increases and decreases in the level of heart rate and HRV may be due to several sources and therefore, it may be only possible to interpret changes in the heart rate level and heart rate variability as being indicative of the activity level of SNS and PNS during controlled situation and preferably with the aid of other measures.

The concept of stress refers generally in physiological domain to a state of heightened level of physiological activity without immediate or apparent requirements for such arousal. In this document, we use the state of stress to indicate a body balance wherein the overall cardiovascular function, as indicated in, e.g., heart rate and cardiovascular output, is substantially higher than the level that is required by immediate physical metabolic requirements. The physiological state of stress may be due to different sources, such as, for example, physical load (e.g., posture), physical condition (e.g., fewer), mental stress, low level of resources (e.g., a burnout condition), or emotional arousal.

It is of note that the detection of stress relates also closely the metabolic processes such as oxygen consumption and caloric consumption, since cardiovascular output indices alone would falsely indicate that metabolic requirements have increased during a state of stress.

Feedback and information on personal stress state and more generally, resources would be very helpful for many individuals to monitor and manage their stress levels, to avoid a state of burnout, and generally to maintain and enhance health condition. Rest and relaxation are important features of stress management, as they help to reduce stress and further buffer and accumulate resources against the onset and adverse effects of stress.

It has been well-documented in the scientific literature that a state of stress is associated with heightened SNS influence to the heart and lowered or diminished PNS influence to the heart (e.g., Porges 1992). It is also known in the prior art that, at rest during steady conditions, relaxation is shown as lowered level of cardiovascular activity and in specific, a decrease in the level of heart rate, and an increase in the magnitude of the HF component of HRV is often found to associate with state of increased relaxation. Some prior work has been documented to take advantage of the role of HR and HRV in stress and relaxation related phenomena (U.S. Pat. Nos. 4,832,038; 4,862,361; 5,891,044; 5,941,837; 6,104,947; 6,212,427; 6,358,201).

Despite this correlational relationship, there has been not very much progress in the detection of stress-related physiological states on the basis of heart period signal. There has been some prior work on using information on heart period and HRV to classify user states, in particular in combination with other physiological measures such as skin temperature. The prior work based on ECG acquisition has been focused mostly on the determination of clinical condition with using specific autonomic nervous system tests and is therefore very limited in their application to characterize behavioral and physiological states in normal life in connection with, for example, ambulatory measurement (U.S. Pat. Nos. 6,358,201, 5,299,199; 5,419,338; 6,390,986; 6,416,473). For example, the work presented by Childre et al ('201) applies heart rate variability parameters in biofeedback context. The described invention is well-applicable to a controlled situation (e.g., in laboratory, relaxation training) but is clearly not applicable to ambulatory monitoring, wherein it would be crucial to differentiate physical and emotional sources of reactions and responses. Accordingly, if used in ambulatory settings one should use a method of manually selecting time periods of, e.g., relaxation training, to the analysis, as the described work does not include any means of separating different types of physical contexts from each other.

There is also some documented work on the use of ECG and heart period derived measures to detect certain physiological conditions, wherein typically one or more parameters are monitored and a threshold limit is set to signal a change in state (U.S. Pat. Nos. 5,267,568; 6,126,595; 6,358,201). These solutions are necessary limited in the content of classifying states and suffer from the fact that the signal value of the heart period and HRV parameters is not always the same but rather, typically varies in combination with physiological states. In other words, they do not account for the state-varying (conditional) relationships between heart period, HRV parameters, and physiological states.

There has been some work on the modeling of state-varying relationships in physiological signals. However, the prior work is typically not related to the determination of stress, may involve heart rate measurement but require the use of two or more physiological measures (U.S. Pat. Nos. 5,810,014; 5,846,206; 5,902,250; 5,921,937). As an example of the above the work of Davis et al. ('014) presents a general approach for a model-based identification of states according to multichannel measurement of raw bio-signals such as electrocardiographic, electromyographic, and electroencephalographic data. The presented system is geared towards the detection of specific abnormal states from physiological waveforms by using a specific model fitting approach. It is obvious to one skilled in the art that the efficiency of the presented state modelling procedure is highly dependent on the availability of repetitive multichannel data, and thus does not apply for the in-depth analysis and decomposition of one signal, such as heart beat, to differentiate specific body states with characteristic dynamics. Furthermore, it should be clear that the described work is clearly not applicable to the analysis of heart beat signal to differentiate states of emotional stress from other sources of body stress.

It is thus clear that, from the point of differentiating different physiological user states and in comparison to the acquisition of only one signal, these approaches require more effort on the measurement of physiological signals and are therefore susceptible to involving more material costs and more restricted user protocols. More importantly, the referred work does not include any contribution to the identification of stress and relaxation, wherein the occurrence of physical activity has not been able to take account in the context of using heart beat signal as the only single input.

As indicated above, the major problem in the operationalization, measurement and monitoring of stress using information on cardiovascular function, such as acquisition of ECG and heart beat, would be the detection and differentiation of the sources of decreased and increased cardiac function. This is especially evident with increased cardiac activity (e.g., as shown by increased level of heart rate and decreased amplitude of HRV), which may result, for example, from increased state of stress, increased state of physical activity, or postural changes.

OBJECTS AND SUMMARY OF THE INVENTION

The object of the present invention is provide an automatic analysis tool for the purposes of providing information on the physiological state of the user on the basis of ECG or heart period measurement. Any method of deriving information on the time difference between subsequent heart beats (e.g., different sensors) may be used to form the necessary input, heart beat signal, for this innovation. More specifically, the object of the invention is to provide a procedure for the differentiation of different physiological states and especially to provide a state-detection based method of deriving a measure of stress on the basis of heart period data. The characteristic features of the invention are disclosed in the accompanying claims.

The invention is based on several computational steps wherein the order of the computations has some constraints. The steps may be characterized as follows: (1) initial transformations of ECG and/or heart period signals; (2) segmentation of the heart period data into stationary segments; (3) detection of the segments associated with other-than-stress related increases in cardiac activity, including physical exercise, physical activity, recovery from physical activity, and postural change; (4) detection of segments characterized by relaxed state; (5) detection of segments containing a potential stress state; and (6) combining information obtained in steps 3-5 to provide an overall index of stress. The procedure may also contain an initial set-up of parameters, such as minimum heart rate, wherein some properties of the state detection system are either inputted or determined automatically.

According to the present system, the detection of stress state is based on the following physiological assumptions: There is sympathetic dominance in relation to the parasympathetic dominance, as indicated in heart beat parameters, and there is no evidence of physical activity, exercise, movement or posture influenced cardiac reactivity.

The invention may be described as an expert system that consists of a sequence of computations and inferences and provides a novel approach to the detection of physiological states and especially stress on the basis of heart beat signal. The types and methods of giving user feedback are dependent on the purpose of the heart beat measuring equipment and software in connection with which the classification and state detection procedure has been applied.

The invention may be applied to and in association with devices such as heart rate monitors and other wearable and mobile computing devices, other types of equipments for physical monitoring and especially involving ECG detection, and software products suited for the analysis of heart period signal. The present invention is useful in combination of any physiological monitoring in the area of monitoring, enhancing and optimizing physiological resources to better manage healthy lifestyle and wellbeing, sports training and fitness, and working capacity. It may be especially useful in the monitoring and providing information on state of stress, where it may be used in the long-term monitoring of the resources, i.e., accumulation and attenuation of stress and resources to deal with stress.

DETAILED DESCRIPTION OF THE PREFERRED EMBODIMENTS

Introduction

The innovation is described here with the aid of an example implementation. It should be noted that the described system is not bound to any specific model or specifications, but rather, different alterations, forms, and improvements are possible and are in line with the spirit of the innovation. Thus, the following merely contains a description of the preferred embodiments of the innovation.

The system involves initially an estimation, input, or use of previously measured parameter values to characterize individual parameter values that influence the detection of states within the system. This estimation of the values is optional for the system. The values may be estimated by using formulas based on empirical data and user-inputted values, such as age, weight, height, and sex. The values may be also based on history values based on empirical physiological measurements, or they may be inputted by the user or expert. Examples of values that may be used on this context are maximum and minimum levels of oxygen consumption, heart rate level, or HRV level.

Figure 1:
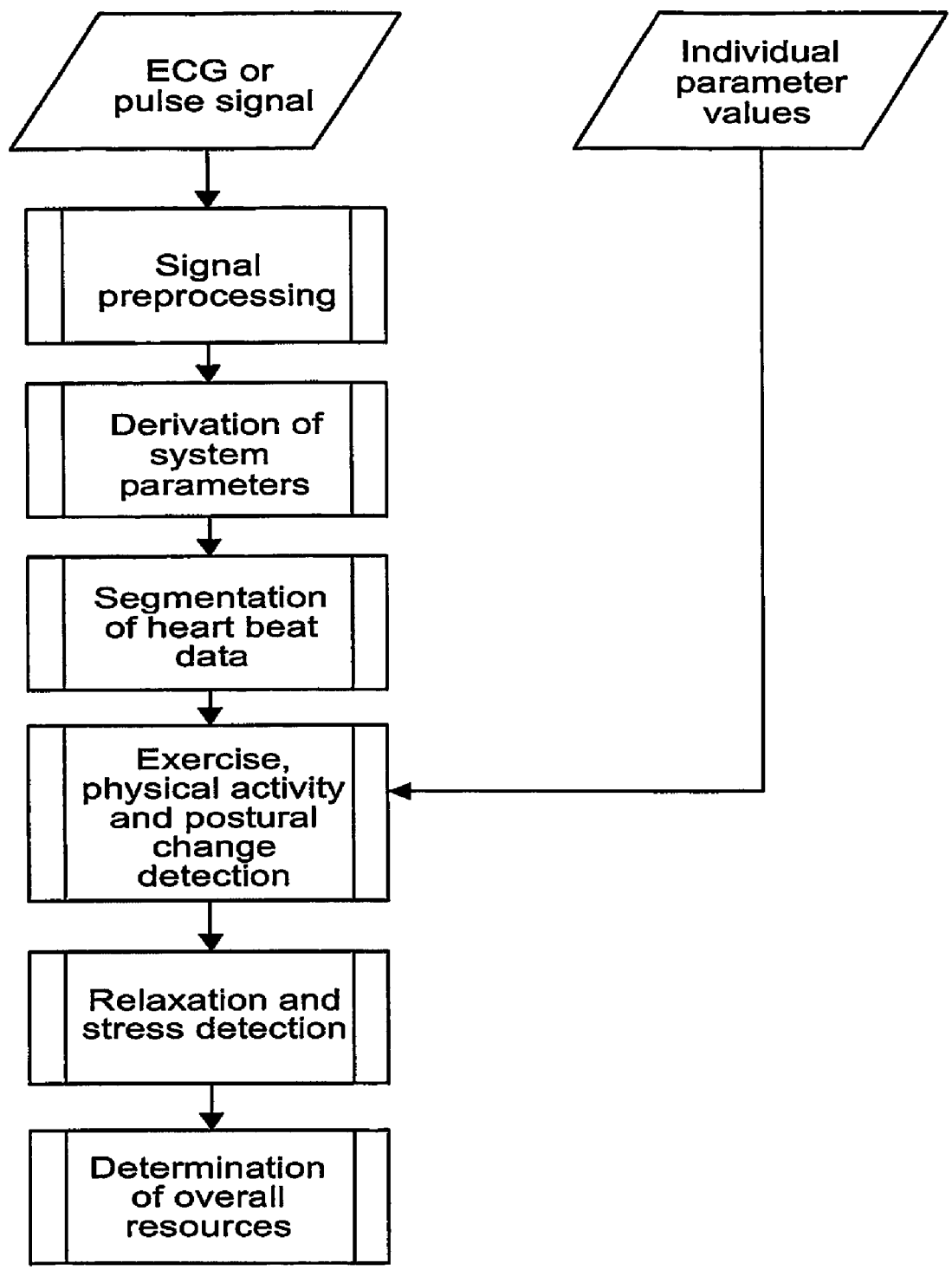
FIG. 1. An overall view of the sequences in the procedure.
Figure 2:
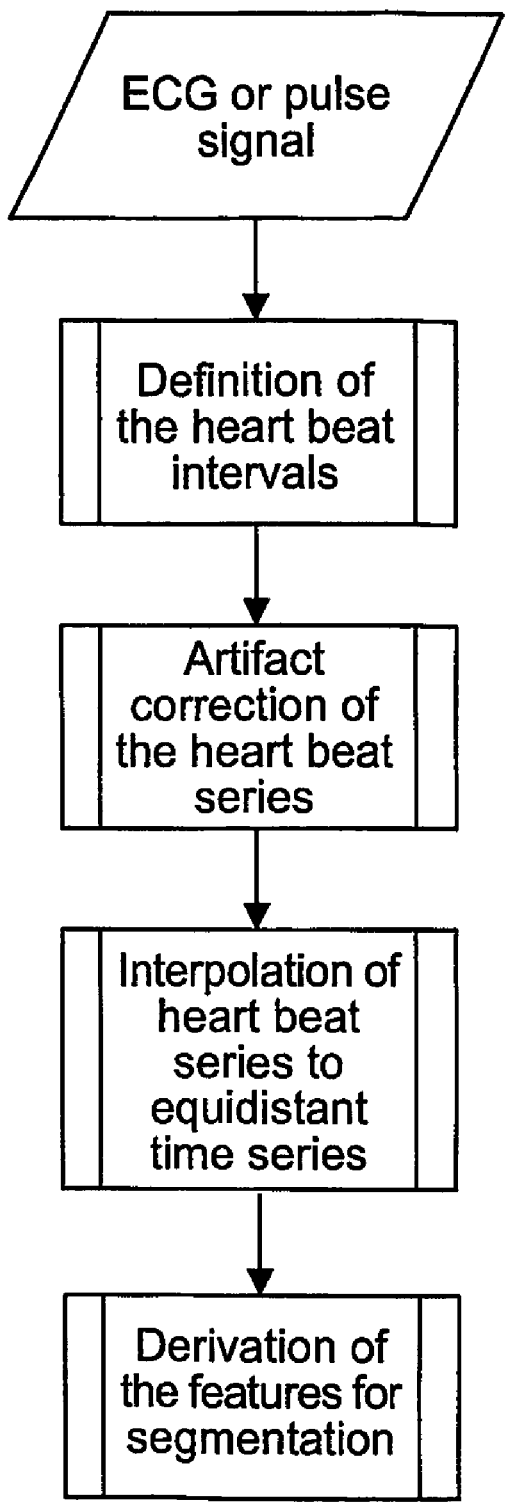
FIG. 2. Initial transformations of the ECG and heart period signal.

FIG. 2 shows an overview of the initial transformations of the ECG and heart period signal. The ECG-signal is transformed into consecutive R-R intervals by using sequential QRS-complexes as markers of the beginning and end of a R-R interval. Also other components of the ECG signal may be used to detect the R-R interval. The consecutive R-R intervals are scanned through an artifact detection filter to perform an initial correction of falsely detected, missed, and premature heart beats. Other potential methods of deriving information on the intervals between consecutive heart beats would be based on the detection of intervals from pulse signal on the basis of different detection algorithms. It should be therefore noted, that in principle, the present innovation applies to all domains wherein temporal information is obtained on the timings between consecutive heart beats.

Consecutive artifact-corrected R-R intervals are transformed into equidistant heart period time series by using a weighted linear interpolation of the R-R intervals. For example, a time domain sampling rate of 5 Hz may be used.

Initial features that may be used in the segmentation of the physiological state of the user into stationary segments are computed prior to the segmentation. The features may include several different components, including the following: spectral power ($ms^2$) in the LF and HF frequency regions, information on respiratory period and ventilation as derived, for example, from the heart period according to Kettunen & Saalasti (PCT/FI03/00426), variation and inconsistencies in respiratory parameters, and oxygen consumption as derived from, for example, heart period and heart period derived respiratory period or ventilation. If available, also external measures of physical activity may be used as a component for segmenting the physiological processes into stationary epochs. All these measures are computed on a continuous basis with preset or dynamically alternating window sizes, thus potentiating the capability for real-time use.

A univariate or multivariate set of features is combined to segment the physiological processes into stationary segments. In other words, the target of the present procedure is to differentiate segments wherein the properties of the physiological system are similar and consistent within-the-segment, using the information obtained from the derived physiological features. An example of an algorithm to perform this is the so-called generalized likelihood ratio test, which basically performs the minimization of the variance within the segments and maximization of the variance between the (consecutive) segments. This process is controlled by threshold parameters that determine the sensitivity of the segmentation process. The use of multivariate set of parameters describing user state is recommended to gain more stability and reliability to the segmentation of data into stationary epochs.

The generalized likelihood ratio (GLR) test is classically applied in model selection but it is also adapted to segmentation algorithms, e.g. the one presented by Fancourt and Principe. In this embodiment the function used to estimate the signal in the segment is median. The error is calculated from the mean absolute error between the median and the signal within segment. For closer details of the algorithm see the article by Fancourt et al. It is clear that the segmentation may be implemented in alternative ways, e.g., with a method described in "The biomedical engineering"; Bronzino, Joseph D, CRC Press, Inc., 1995.

Generally segments are defined from heart beat signal with a chosen rule (e.g. Francourt) for segmentation, and at least one segment describing a physiological state with elevated cardiac activity due to physical workload and/or increased metabolic rate is identified (e.g. eq. 1) ) and excluded, if exists, and segments other than the excluded segments are detected for a potential stress state, which is identified using a predetermined rule for the heart beat signal (e.g. eqs. 3 and 4). In a simple manner the segmentation uses so called moving window method with predefined window length.

Figure 3:
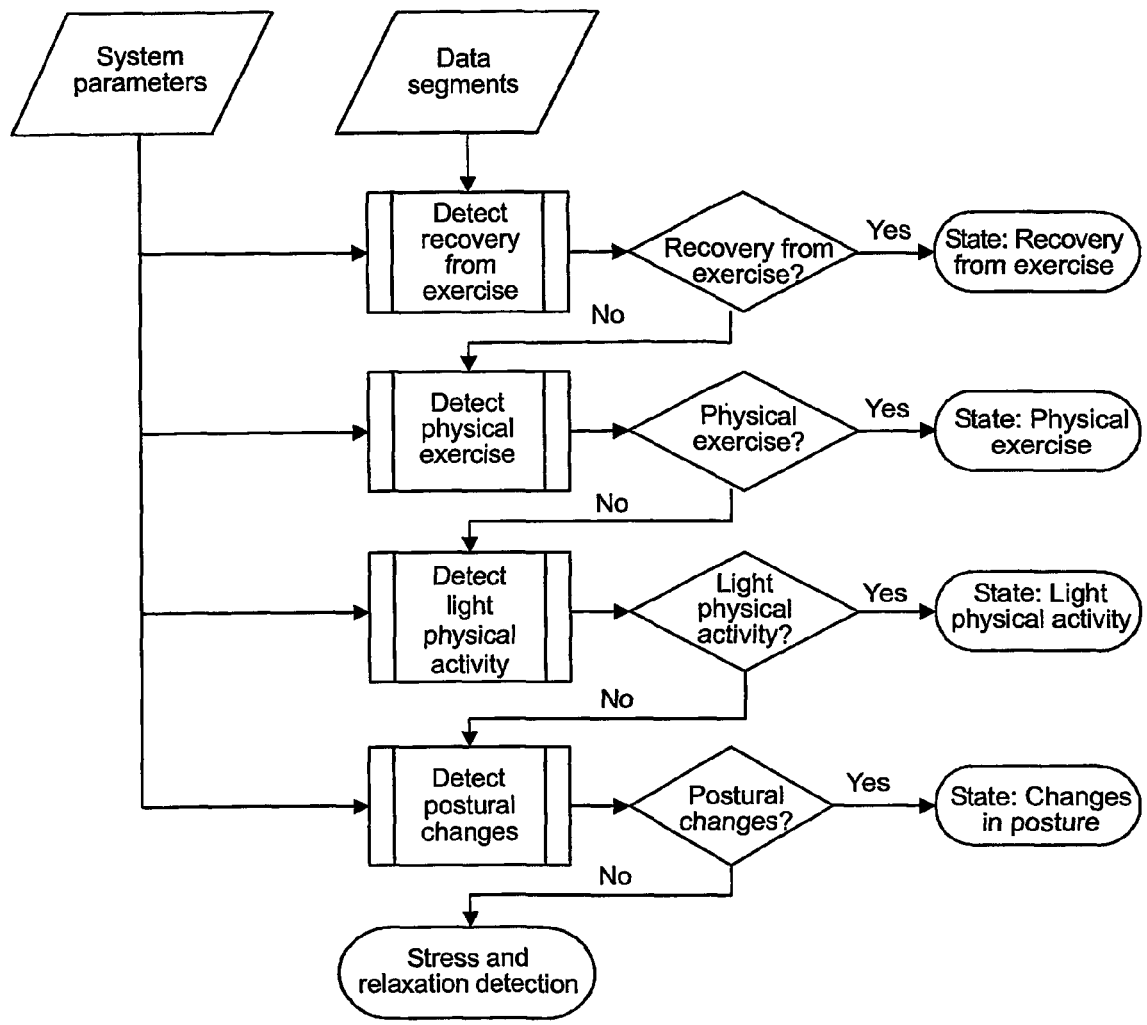
FIG. 3. An illustration of the procedure for the detection of exercise, recovery from exercise, physical activity, movement and postural changes.

In the following the procedure for detecting physiological state is presented. Selected physiological parameters are analyzed from each stationary segment to form a basis for inference on states that include increased cardiac activity. The detection of physical activity (i.e., metabolism related) induced states of increased cardiac reactivity is done and those segments are excluded before the detection of potential states and intensities of relaxation and stress. FIG. 3 presents a flowchart on the procedure of detecting physical activity related states.

Increased level of cardiac activity (e.g., increased heart rate level or decreased heart period level) may be due to the process of recovering from physical exercise or from any physical activity. The state of recovering from exercise may be detected by, for example, applying the method described in Saalasti, Kettunen, Pulkkinen; patent applications FIN 20025038, PCT, to determine the level of recovery requirements in the body and classify segments involving recovery demands higher than a certain predetermined threshold as recovery state.

The system requires information on the intensity of physical activity and exercise to differentiate exercise related effects on cardiac system from, e.g., stress related effects. The transformation of heart beat level into proportional intensity of physical activity is done by applying for example information on the relationship of heart rate level to oxygen consumption. It is a very practical way to determine oxygen consumption from heart rate and external input, e.g. accelerator and then using the derived value of oxygen consumption to determine whether physical load exists (not a stress state). This external input may comprise one or more sensors detecting movement, such as accelerometer or simply it can be manual input.

It is possible also to use information on initial parameters, such as maximum and minimum levels of heart rate and oxygen or energy consumption and heart rate variability to increase the accuracy of determining the intensity of physical activity. However, it is clear that the direct transformation of heart level to exercise intensity does not produce optimal results for the purposes of differentiating other-than-exercise related increase in cardiac activity from exercise induced reactivity.

The estimate of the proportional intensity of physical activity may be enhanced by including information on the respiratory period and ventilation, as obtained, e.g., from heart period. Furthermore, given that exercise has also certain pattern of changes in respiratory activity (e.g., exercise is associated with increased respiration, whereas other-than-exercise related cardiac reactivity is not often associated with similar respiratory reactivity) and HRV (e.g., a certain level of HRV is typically associated with certain level of heart rate during exercise), and temporal length (i.e., exercise and intensive physical activity is necessarily bound to have a certain temporal length). It would be also possible to use external sensors to detect the occurrence and intensity of movement and physical activity with, for example, accelerometer or skin temperature sensors, location, distance, ventilation, or oxygen consumption, to support the determination of exercise intensity related changes in heart beat signal.

A certain threshold value is preset to determine whether a certain segment involves exercise or intensive physical exercise. Given that no other reasons related to respiration, HRV, or temporal length of increased heart rate provides evidence that a potential exercise induced increase in cardiac activity is not associated with intensive physical activity, segments containing a mean intensity of physical activity higher than, for example, 50% of exercise intensity may be classified as intensive exercise.

Movements, start-up of a physical activity, and postural changes have all metabolic requirements and they also increase heart rate level. It is thus necessary to differentiate these effects from other, non-metabolic factors influencing cardiac activity. It is known that PNS often controls increase in cardiac activity at the onset of movement and decrease in cardiac activity at the end of movement. It is also known that standing up, which poses a so-called orthostatic reaction, is associated with increase in the spectral power in the LF frequency region of HRV in relationship to HF power, which usually decreases when standing up. Based on these assumptions, a covariance parameter according to Equation 1 has been derived to index movement related changes in cardiac activity. "E" denotes an average value.

$$\text{movement} = \alpha \cdot cov(\log(HFpow)) + E\left(\frac{LFpow}{HFpow}\right) \quad \text{Equation 1}$$

An increase in the level of the described parameter indicates the prevalence of movement related increases in cardiac activity and thus may be used to differentiate states of movement, onset and offset of physical activity, and postural changes. When this exceeds preset threshold value, physical activity is detected.

Information on the derivative of heart rate or heart rate variability is used as an indicator of movement induced cardiac reactivity. Relatively fast increase and decrease of heart rate level indicates physical load (not a stress state).

The detection of light physical activity is similar to that of intensive physical activity but the threshold values are different. However, the detection of light physical activity differs from that of detecting intensive physical activity in that it is expected that metabolic demands are substantially lower and thus related changes in cardiac activity also different. In other words, the co-variance term introduced in Equation 1 is used to differentiate light physical activity related increases in metabolism from cardiac reactivity that is due to different sources. It is also here of note that, in a similar manner to the intensive physical activity, additional sensors detecting movement occurrence and intensity could be also used as a source of information to differentiate heart beat segments that include light physical activity.

The detection of movement and reactivity due to changes in posture is performed by using the covariance term presented in Equation 1 with preset threshold values and a period surrounding the covariance. The covariance term may be smoothed with, for example, a Hanning window.

In general, it is known that exercise, physical activity, and movement all have their typical time frames that have minimal temporal requirements for recovery. For this purposes, it may be possible to use a frequency or time domain measure to provide information on the temporal properties of the changes in cardiac activity, thus potentiating the comparison of those with those typical in the case of different types of physical activity.

It is important to notice that, for example, as the changes in the heart rates during physical activity are associated with several different types of changes, these changes may be combined in an automatic decision function that may be, for example, deterministic, heuristic, or based on multi-variate methods such as fuzzy systems and neural network.

In one embodiment, the information on whether the heart rate segment is or is not detected as having increased physical load such as movement or postural changes is used as an information in a model that determines oxygen consumption or energy consumption level on the basis of heart rate information. In its simplest form, the formula predicting oxygen consumption or energy consumption level would be conditional to the information on the segment, so that a different formula or a correction factor would be used depending on whether the segment would be defined as having movement or other form of physical load. In another terms, given that stress and movement both alter cardiac activity and yet have different metabolic responses, the information obtained with the present innovation may be applied to the context of evaluating metabolic processes.

It is emphasized that in this embodiment both the oxygen and energy consumption may be utilized in the detection process. Furthermore, a movement sensor may give further information and provide improved detection for the segmentation of physical load from heart beat signal, and thus may improve both oxygen and energy consumption estimation. It should be clear there may be also other applications.

Figure 4:
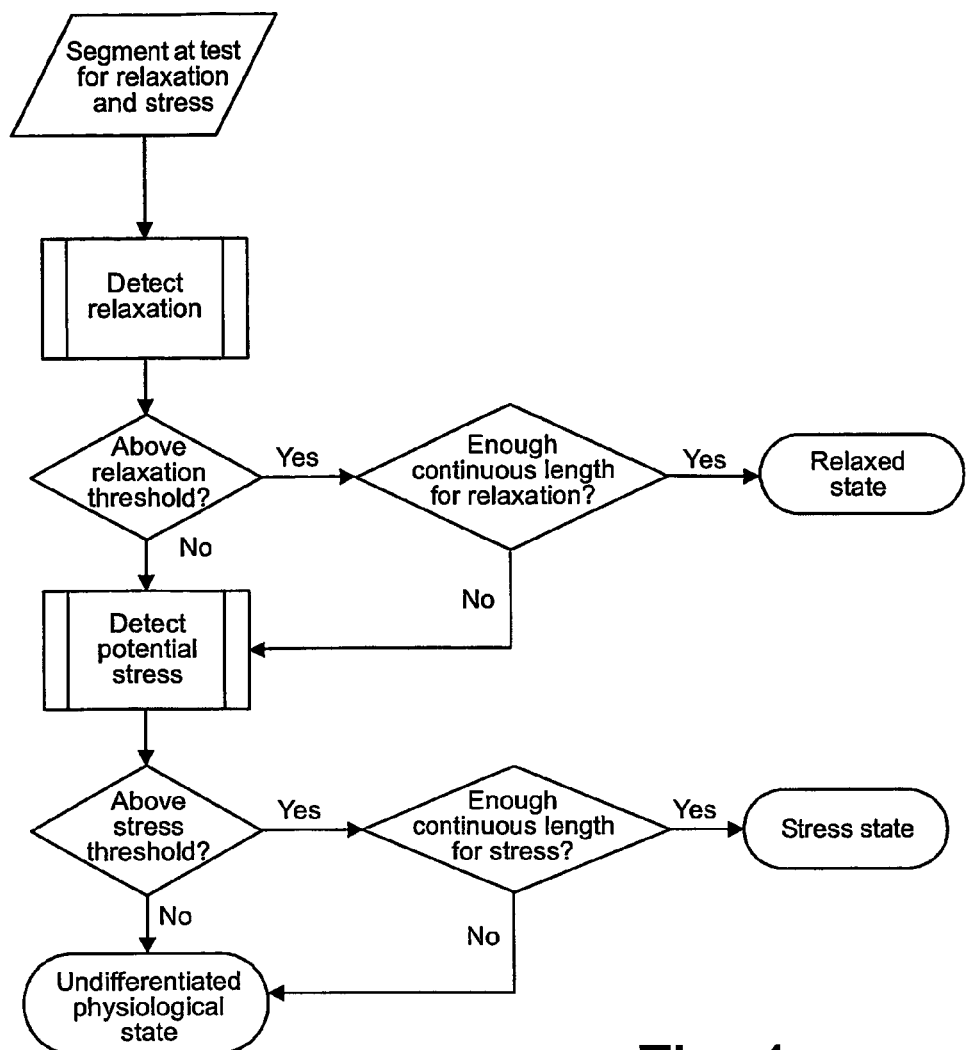
FIG. 4. Procedure for the detection of relaxation, stress state, and combination of information to describe overall body resources FIG. 5. Example of the detected periods of stress and relaxation states during a measurement period FIG. 6. Example of accumulated resources during workday

FIG. 4 shows an overall view on the detection of relaxation and stress. Relaxation index for the segment is determined by the combination of heart period and HF power as illustrated in Equation 2.

The LF- and HF power estimates may be calculated with, e.g., short-time Fourier transformation (a.k.a. Gabor transformation), providing a generalization of a stationary Fourier into nonstationary time series analysis. Also Cohen-class of time-frequency distributions may be utilized, e.g., smoothed pseudo Wigner-Ville transformation, or time-scale presentations, e.g., Wavelet transformation. Furthermore, to improve system accuracy and behavior the signal may be altered with several digital signal processing steps, e.g., digital filtering, artifact detection and correction, de-trending, logarithmic transformations or signal scaling and normalization.

$$RLXpow = E\left(\frac{HFpow}{HR}\right) \qquad \text{Equation 2}$$

The relaxation power may be detected, e.g., by calculating a mean HF power respect to heart rate inside the detected segment. A hard limit threshold may be defined to declare the reasonable function range for relaxation by exploiting the knowledge of the scale of the variables used in the calculus, e.g., a threshold proportional to minimum and maximum heart rate and HF power. An example relaxation power is presented in Equation 2.

If no relaxation state is detected, the data segment is a potential candidate of including stress. Equation 3 shows an example of how an index of stress may be computed inside the segment. In Equation 3, HR denotes heart rate level, CT denotes inconsistencies in the frequency distribution of HRV due to changes in respiratory period, or alternatively, variability in the respiratory signal. HFpow and LFpow denote spectral powers in the HF and LF regions of the HRV, respectively.

$$STRpow = E\left(\frac{HR \cdot CT}{HFpow \cdot LFpow}\right) \qquad \text{Equation 3}$$

It should be clear to anyone familiar with the field that the formula presented for computing stress index is only illustrative and may be formed in several methods. Both indices shown in Equations 2 and 3 may take different forms. Both indices may be also used to derive continuous parameters, which may be useful in some contexts of deriving overall, long-time information on stress and relaxation.

The principle is to search for periods of increased heart rate with other markers of potential stress and related in general to heightened level of SNS activity and diminished level of PNS activity. The rate of recovery of heart rate and/or heart rate variability from state of increased cardiac activity may be also used as an indicator low level stress and high level resources.

The indices of relaxation and stress may be combined taking advantage of the proportion of different states and the intensity of relaxation and stress states. An example of such combination is presented in Equation 4.

$$\text{Total\_resources} = c_1 \cdot \frac{T_R}{T} \cdot RLXpow - c_2 \cdot \frac{T_S}{T} \cdot STRpow \qquad \text{Equation 4}$$

where $c_1$ and $c_2$ are constants, T is total time of the measurement or a reference time, e.g., 24 hours, $T_R$ is time classified as relaxation, $T_S$ is time classified as stress, RLXpow the intensity of relaxation, which may be scaled in absolute values or proportional to maximal value, for example, and STRpow is the intensity of stress state (see the computation of stress index in Equation 3), which also may be scaled in absolute values or in proportion to the maximal value. The intensities may be calculated via mean or median values of the corresponding time series indices. The combined index may be especially useful in the comparison of different days. The constant $c_1$ and $c_2$ may be used to scale the stress and relaxation intensities to each other.

Figure 5:
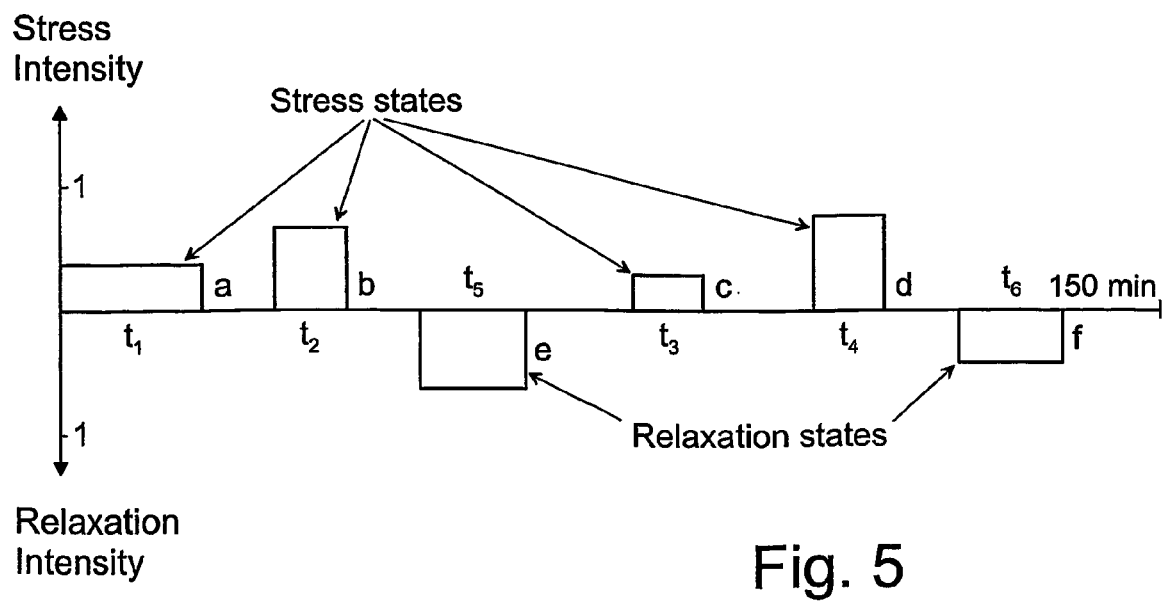

FIG. 5 demonstrates a simplified example of the detected periods of stress and relaxation states during a measurement period. Note that information is gained on both the intensity (denoted as fixed constants a-f in the figure) and length (e.g., duration) of relaxation and stress periods. The time periods that are not detected as either stress or relaxation are either excluded from the analysis as having exercise or other types of increased physical load, or are not excluded from the stress analysis but are not detected as containing either stress or relaxation state.

An example of using the equation 4 with data presented in FIG. 5. In this example the level of RLXpow and STRpow are both pre-scaled between 0 and 1, that is, proportional to their maximal and minimal values. The maximal and minimal values may be either inputted or detected from the data. If non-scaled values would be used the constants $c_1$ and $c_2$ could have substantially larger or smaller values to account for, for example, logarithmic differences in the scales of STRpow and RLXpow.

$$\text{Total\_resources} = 1 \cdot \frac{50}{150} \cdot 0.50 - 2 \cdot \frac{30}{150} \cdot 0.30 \approx 0.047$$

where RLXpow=average(e, f) relaxation intensities and STRpow=average(a, b, c, d) stress intensities In principle, a segment is identified as stress if heart rate is constantly at a high level and it is apparent that it is caused by lowered level of PNS, higher level of SNS, and there is no evidence of physically determined heart rate reactivity. In fact, given that stress is associated with a tonic low level of PNS and that high level of PNS potentiates reactivity, the absence of PNS mediated responses is also an indicator of stress and may be taken more formally into account. If a person is highly stressed, it may not be possible to find states of relaxation even during long periods.

Feedback on the results of the present procedure may be presented to the user either on real-time application or off-line, after the measurement. It is possible to give feedback on states, on relaxation and stress components, and overall resources. The feedback may be given in many forms, for example, in graphics or as a single parameter that is easy to interpret.

There are several methods of setting up the stress quantification procedure to account for accumulative and dynamic changes in stress state. The accumulation of stress level (and, relaxation) may be determined as follows, Accumulated\_stress$_t$=Accumulated\_stress$_{t-1}$+$f$(Accumulated\_stress$_{t-1}$, Stress\_level$_t$)

The same kind of methods may be also used in the case of available resources, which may both increase (i.e., more relaxation than stress) and decrease (i.e., more stress than relaxation). For this purposes, it may be useful to determine the change in resources according to, in general, following, Change\_in\_resources$_t$=$f$(stress\_level$_t$, relaxation\_level$_t$), wherein stress\_level$_t$ and relaxation\_level$_t$ may be determined by STRpow$_t$ and RLXpow$_t$, respectively.

In its simplest form, changes in resources may be determined as

Change\_in\_resources$_t$=relaxation\_level$_t$−stress\_level$_t$, in particular if the stress and relaxation levels are scaled between 0 and 1. In this example of scaling, the decrease in resources due to stress would be at its maximum comparable to the increase due to resources at its maximum.

The accumulation of resources due to momentary decreases and increases in resources may be determined as follows, Accumulated_resources$_t$=Accumulated_resources$_{t-1}$+$f$
(Resources$_{t-1}$, Change_in_resourses$_t$).

Figure 6:
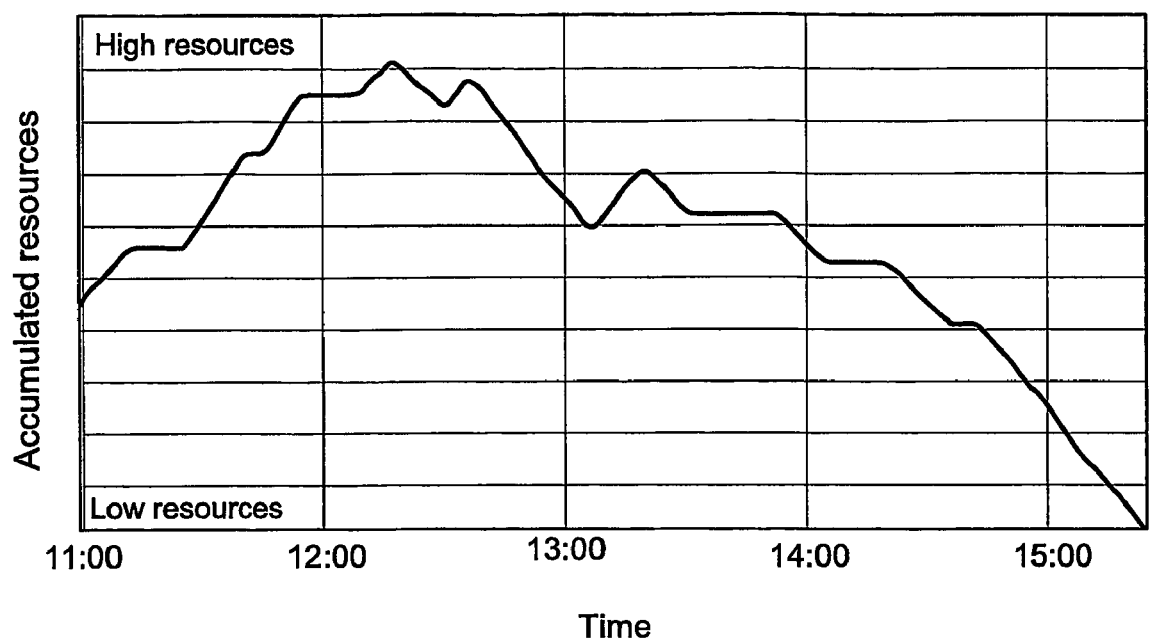

FIG. 6 demonstrates the product of a calculation of accumulated resources, wherein relaxation increases resources and stress state decreases accumulated resources. In this particular example stress level and relaxation level are scaled as proportional to their maximum.

One inherent benefit of the accumulated index is in its capacity to describe the accumulated dynamics in stress and resources usage. Another, very significant benefit of accumulated index is in its use to scale the accumulation of stress and resources usage according to a pre-determined scaling.

It is possible to scale the relaxation and stress components to satisfy a pre-defined criteria in terms of resources usage. For example, the parameters can be set according to a scaling that it would take a period of 150 minutes to recover, at full relaxation level, from stress state that would have been acquired, with full stress level, in only 75 minutes. Another pre-set criteria may influence the accumulation of stress level and accelerated use of resources, wherein history information on accumulated stress state may further magnify the effects of present stress state to further accelerate the use of available resources.

Yet another possible scaling may be used to relate the accumulation and use of stress and/or resources to a scale that describes a probability that a particular accumulated stress or resources state would have healthy or unhealthy physical consequences.

Implementations of the invention can be a computer software in a personal computer, a heart rate monitor (wrist top computer), ECG-monitoring or pulse monitoring equipment such as a cardiac pace maker and an ergometer (a stationary bicycle) or other fitness exercise equipment. Generally an implementation consists of a processing unit, a terminal, software and at least one input device.

The invention claimed is:

1. Procedure for the detection of stress state associated with body balance wherein the overall cardiovascular function is substantially higher than immediate physical metabolic requirements, the procedure comprising the steps of:
measuring an ambulatory heart beat signal,
defining segments from said heart beat signal with a first chosen rule for segmentation, and
identifying and excluding at least one segment describing a physiological state with elevated cardiac activity due to physical workload and/or increased metabolic rate, if exists, and
detecting segments other than the excluded segments for a potential stress state, which is identified using a predetermined second chosen rule for the heart beat signal.

2. Procedure according to claim 1, including the step of using the first chosen rule to identify state and period of one or more following: exercise, physical activity, movement, recovery from exercise and postural changes.

3. Procedure according to claim 1, wherein the second chosen rule comprises a procedure to identify internally coherent segments from said heart beat signal.

4. Procedure according to claim 1, including the step of using detected segments for correcting heart rate based oxygen- and energy consumption estimate.

5. Procedure according to claim 1, including the step of determining an index representing a summary of the existence and level of stress, relaxation and/or resources for a chosen period of measurement.

6. Procedure according to claim 1, including the step of measuring stress and relaxation on the basis of heart period measurement, wherein information on the length of detected relaxation and length of detected stress is used as informative in the detection and quantification of relaxation and stress states.

7. Procedure according to claim 1, including the step of obtaining information on the exercise, physical activity, movement, or postural changes from said heart beat signal and at least one separate input.

8. Procedure according to claim 1, wherein the stress state is defined with the formula:

$$STRpow = E\left(\frac{HR \cdot CT}{HFpow \cdot LFpow}\right)$$

wherein HR denotes heart rate level, CT denotes inconsistencies in the frequency distribution of HRV due to changes in respiratory period, or alternatively, variability in the respiratory signal, and HFpow and LFpow denote spectral powers in the HF and LF regions of the HRV, respectively.

9. Procedure according to claim 1, wherein the procedure comprises the calculation of a relaxation index a relaxation index defined by the formula:

$$RLXpow = E\left(\frac{HFpow}{HR}\right)$$

wherein HR denotes heart rate level, and HFpow denotes spectral powers in the HF regions of the HRV.

10. Procedure according to claim 1, wherein the procedure comprises the calculation of a total resources index a total resources index defined by the formula:

$$\text{Total\_resources} = c_1 \cdot \frac{T_R}{T} \cdot RLXpow - c_2 \cdot \frac{T_S}{T} \cdot STRpow$$

where $c_1$ and $c_2$ are scaling constants, T is total time of the measurement, Tr is time classified as relaxation, Ts is time classified as stress, RLXpow is the intensity of relaxation state and STRpow is the intensity of stress state.

11. Procedure according to claim 1, wherein the procedure is used in a wearable computer.

12. Procedure according to claim 1, wherein the procedure is used in a fitness exercise equipment.

13. Procedure according to claim 1, wherein the procedure is used in a PC-software.

14. Procedure according to claim 1, wherein the procedure is used in a ECG/pulse-monitoring equipment.

* * * * *